(12) United States Patent
Baglini

(10) Patent No.: US 10,398,340 B2
(45) Date of Patent: Sep. 3, 2019

(54) DEVICE AND METHOD FOR NON-INVASIVE RECORDING OF THE ERG AND VEP RESPONSE OF AN EYE

(71) Applicant: COSTRUZIONI STRUMENTI OFTALMICI C.S.O. S.R.L., Scandicci (FI) (IT)

(72) Inventor: Claudio Baglini, Migliarino Pisano (IT)

(73) Assignee: COSTRUZIONI STRUMENTI OFTALMICI C.S.O. S.R.L., Scandicci (FI) (IT)

( * ) Notice: Subject to any disclaimer, the term of this patent is extended or adjusted under 35 U.S.C. 154(b) by 0 days.

(21) Appl. No.: 15/562,968

(22) PCT Filed: Apr. 6, 2016

(86) PCT No.: PCT/IB2016/051936
§ 371 (c)(1),
(2) Date: Sep. 29, 2017

(87) PCT Pub. No.: WO2016/162796
PCT Pub. Date: Oct. 13, 2016

(65) Prior Publication Data
US 2018/0110437 A1  Apr. 26, 2018

(30) Foreign Application Priority Data

Apr. 7, 2015 (IT) ................. FI2015A0103

(51) Int. Cl.
*A61B 3/00* (2006.01)
*A61B 3/14* (2006.01)
(Continued)

(52) U.S. Cl.
CPC .............. *A61B 5/0496* (2013.01); *A61B 3/12* (2013.01); *A61B 5/04842* (2013.01);
(Continued)

(58) Field of Classification Search
CPC ......... A61B 3/1015; A61B 3/103; A61B 3/14; A61B 3/113; A61B 3/1208; A61B 3/1225;
(Continued)

(56) References Cited

U.S. PATENT DOCUMENTS

2007/0239063 A1* 10/2007 Narfstrom ............ A61B 5/0496
600/558
2015/0342495 A1* 12/2015 Davis ....................... A61B 3/12
351/221

FOREIGN PATENT DOCUMENTS

| WO | 9012534 A1 | 11/1990 |
| WO | 2010006180 A1 | 1/2010 |
| WO | 2014117154 A1 | 7/2014 |

OTHER PUBLICATIONS

International Search Report and Written Opinion for International Application No. PCT/IB2016/051936 (8 Pages) (dated Jul. 6, 2016).

* cited by examiner

*Primary Examiner* — Dawayne Pinkney
(74) *Attorney, Agent, or Firm* — Lucas & Mercanti, LLP

(57) ABSTRACT

The present invention refers to the field of ophthalmology, and in particular to that of devices and methods for supporting the diagnosis of important eye pathologies such as Age-related Macular Degeneration (AMD), Diabetic Retinopathy (DR), anomalies and dysfunctions of the retina and of sight in general such as degeneration of the retinal structure of the optical nerve and of the visual cortex. More specifically, the invention concerns a new device and method for recording the electroretinogram (so-called ERG) of an eye, i.e. the bioelectric response of the retina induced by a light stimulus, through the eyelid.

7 Claims, 2 Drawing Sheets

(51) Int. Cl.
*A61B 3/02* (2006.01)
*A61B 5/04* (2006.01)
*A61B 5/0496* (2006.01)
*A61B 5/00* (2006.01)
*A61B 3/12* (2006.01)
*A61B 5/0484* (2006.01)
*A61B 3/113* (2006.01)
*A61F 9/007* (2006.01)

(52) U.S. Cl.
CPC ............ *A61B 5/7228* (2013.01); *A61B 3/113* (2013.01); *A61F 9/007* (2013.01)

(58) Field of Classification Search
CPC ......... A61B 3/024; A61B 3/18; A61B 5/0408; A61B 5/04085; A61B 5/0478
USPC ....... 351/246, 200, 205, 206, 209, 210, 220, 351/221, 222, 245; 600/372, 383, 382
See application file for complete search history.

DEVICE AND METHOD FOR NON-INVASIVE RECORDING OF THE ERG AND VEP RESPONSE OF AN EYE

CROSS-REFERENCE TO RELATED APPLICATIONS

This application is a 371 of PCT/IB2016/051936, filed Apr. 6, 2016, which claims the benefit of Italian Patent Application No. FI2015A000103, filed Apr. 7, 2015.

FIELD OF THE INVENTION

The present invention refers to the field of ophthalmology, and in particular to that of devices and methods for supporting the diagnosis of important eye pathologies such as Age-related Macular Degeneration (AMD), Diabetic Retinopathy (DR), anomalies and dysfunctions of the retina and of sight in general such as degeneration of the retinal structure of the optical nerve and of the visual cortex. More specifically, the invention concerns a new device and method for recording the electroretinogram (so-called ERG) and the visual evoked potential (so-called VEP) of an eye, i.e. the bioelectric response of the retina induced by a light stimulus, through the eyelid in a non-invasive manner.

BACKGROUND OF THE INVENTION

The recording of the bioelectric responses generated by the retina as a consequence of a visual stimulus perceived by the patient is a remarkably useful tool in order to support the medical operator in diagnostic activity. The aforementioned bioelectric responses are recorded, through suitable electrodes arranged at the level of the conjunctival fornix, the corneal one, or close to the central visual cortex by means of surfaces electrodes (of both eyes in the case of binocular recording), from which an electric biopotential is then obtained. This represents a measurement of the integrity of the visual system (density of cones, rods and cells connected to them, ganglion cells, retinal cells, nerve fibres and visual cortex) or of possible alterations or destructive actions already caused by the various pathologies.

With current techniques (ISCEV Standard for full-field clinical electroretinography—2008 update—M. F. Marmor et al.) ERG and VEP recording is obtained by stimulating the retina and the optical nerve through the dilated pupil, with adaptation of the retina itself to the dark (scotopic condition) or to light (photopic condition). The light stimuli according to this technique are emitted by a lambertian surface having homogeneous intensity (constant luminosity) distributed over the entire visual field of the patient. By effect of the dioptric elements of the eye (cornea and crystalline lens) the light stimulus is distributed through the dilated pupil over the entire surface of the retina. The correction of the photometric measurement of the luminosity values that impact on the eye, scaling them with the actual measurement of the pupil, is carried out according to the Troland unit.

Although widely used, this technique has some limitations, the first of which is the invasiveness due to the insertion of electrodes (the sensors used for recording the bioelectric activity of the retina) in contact with the eye. There is also uncertainty of the measurement due to the difficulty for the patient in keeping his/her eye open during the examination. The possible contamination and transmission of infective diseases deriving from contact with electrodes not properly disinfected should also be mentioned; avoiding this obviously involves slowing everything down when numerous patients must be examined in sequence, since careful cleaning must indeed be carried out between one patient and the next.

SUMMARY OF THE INVENTION

The purpose of the present invention is to overcome the aforementioned drawbacks by providing a device and a method for recording the ERG and VEP response of an eye which result in examinations that are more reliable, faster and less invasive with respect to the prior art.

Such a purpose is accomplished by the device for recording the ERG and VEP response of an eye through the eyelid according to the invention the essential characteristics of which are defined by the first of the attached claims. A corresponding method is essentially defined by what is specified in claim 9.

The device and the method according to the invention are adapted for implementing an improved technique that provides for recording the ERG and VEP through the eyelid and therefore with the eye closed, eliminating the invasiveness of the electrodes in contact with the eye surface. Concerning this, it should be noted how according to current reference standards for medical devices, the eye surface is considered an orifice or stroma of the human body. On the other hand, the eyelid is considered as the epidermal surface, so that simple contact with it, indeed according to the invention, achieves a totally non-invasive condition, contrary to the prior art.

By keeping the patient under examination with eyes closed during the examination, the intrinsic measurement uncertainty linked, in the prior art with open eye tests, to the natural tendency for the patient to blink during the test is avoided. The device according to the invention is also more suitable, for obvious reasons, for carrying out examinations on paediatric patients. A further advantage of the technique according to the invention derives from the reduction of the risks of contamination. The electrodes rested on the outside of the eyelids indeed do not normally come into contact with organic fluids and therefore their cleaning, even where it is judged suitable for absolute safety and hygiene, can be carried out with maximum ease and speed. This also leads to the possibility of examining a large number of patients very quickly.

BRIEF DESCRIPTION OF THE DRAWINGS

The characteristics and advantages of the device and method for recording the ERG and VEP response of an eye through the eyelid according to the present invention will become clearer from the following description of an embodiment thereof, given as an example and not for limiting purposes with reference to the attached drawings, in which.

DETAILED DESCRIPTION OF THE INVENTION

Figure 1:
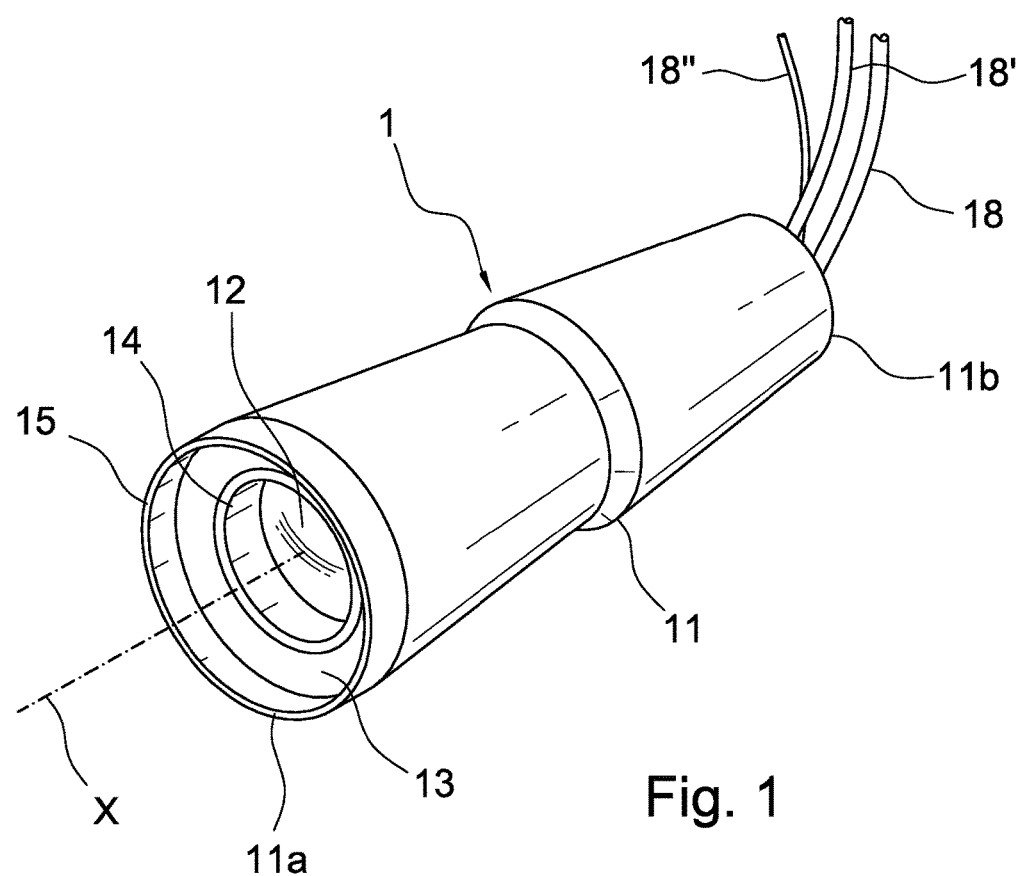
FIG. 1 shows a perspective view of a device according to the invention in a generic mechanical configuration.
Figure 2:
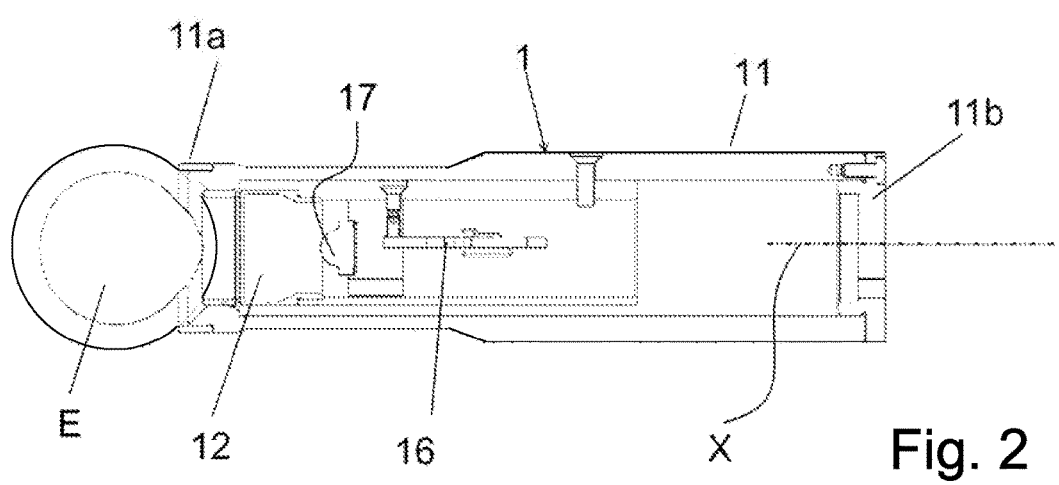
FIG. 2 is a section view of the device of FIG. 1.
Figure 3:
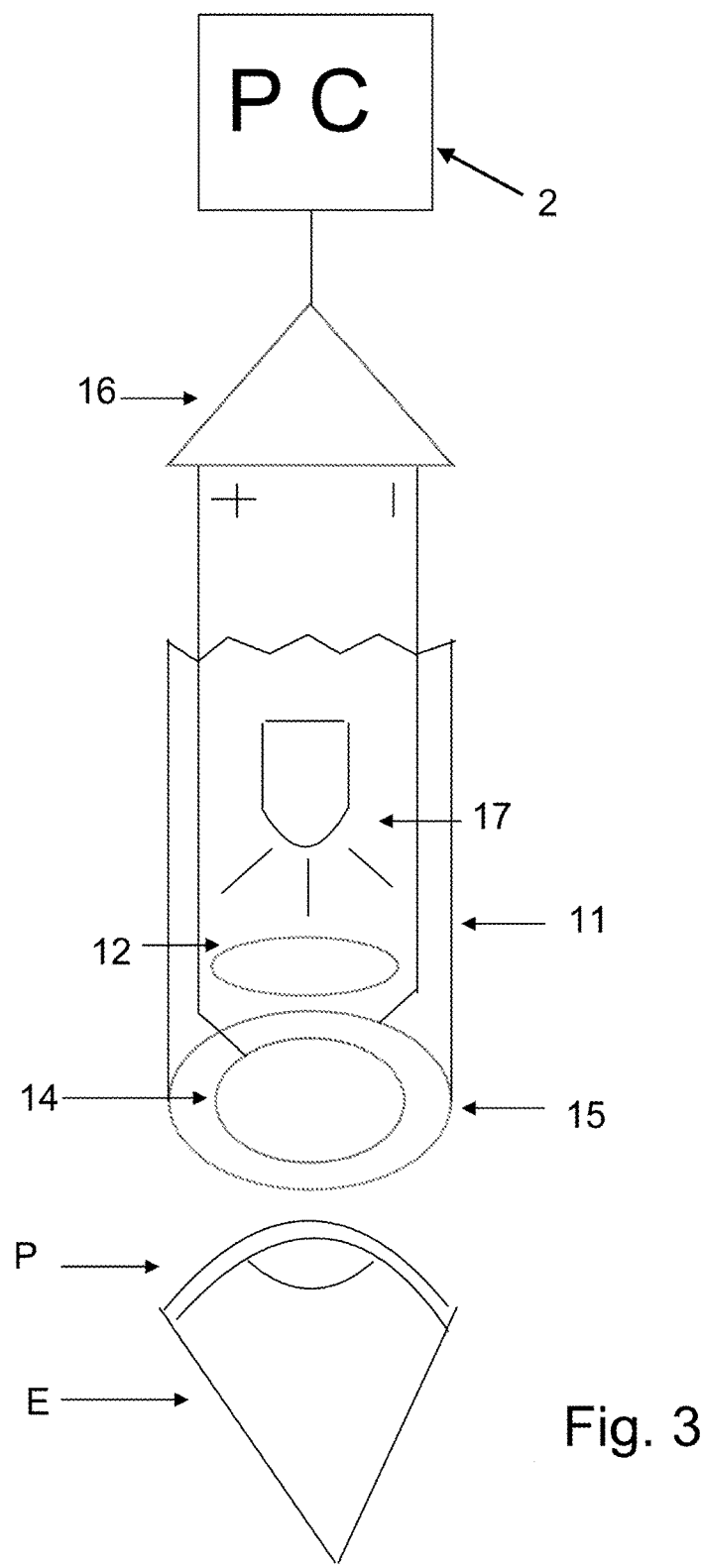
FIG. 3 schematically represents the device with its main components.

With reference to said figures, a device according to the invention comprises a handpiece 1 adapted for being gripped by a medical operator. For this purpose it has a tubular case 11, preferably ergonomically shaped and of tubular structure of substantial axial symmetry about an axis X and of diameter substantially corresponding to the average or standard eye socket of an adult patient (possibly handles of different sizes can be provided for better adaptation of the handpiece to different patients, in particular with respect to paediatric patients).

Along the aforementioned axis two ends of the case 11, and therefore of the handpiece 1, are defined. A first end 11a or front end is that intended to make contact with an eyelid P of a patient's eye E; opposite the first end, a second end or rear end 11b is defined, at which the case 11 is blind and it is possible there to arrange for the connection of one or more wires 18, 18', 18" for the transmission of power and signal, which place the handpiece in communication with control processing means 2. The wire connection can obviously be replaced by a wireless communication, and for the power supply it is possible to use a battery on-board the handpiece.

At the front end 1a the case 11 is open, with the opening being shut by a lens 12. Around the lens 12, and therefore along the perimeter of the opening, a ring 13 evolves that is intended for abutting and therefore for making contact with the patient's epidermis, in particular around the eye socket and therefore for at least a portion on the closed eyelid. At least one such a portion an active electrode 14 is arranged in the ring 13, said electrode being of a per se analogous type to those for the corneal contact of the systems for recording the ERG response already known and cited in the introductory part. The ring 13 and the lens 12 in practice make an eyepiece for bringing up to the closed eye E of the patient.

Again on the ring, but in a more peripheral position, i.e. radially more outer, there is also a reference electrode 15. The two electrodes are connected, according to a circuit configuration that should in turn be considered similar to that of known systems, with a differential amplifier 16 the output of which represents the detection signal that, processed by the processing means 2 with which the amplifier is connected for example through a wire 18, carries out the recording to the biopotential. Such a differential amplifier is indeed characterised by an appropriate pass band and by an amplification factor adapted for recording the aforementioned bioelectric activity of the retina. As an example, the pass band used can consist of a lower cutting frequency (filter PA) at 10 Hz and upper cutting frequency (filter PB) at 100 Hz. Such a pass band is optimised for the detection of the bioelectric activity of the retina following light stimuli at a frequency of 30 Hz with a duration of the stimulus of 5 ms. An analogue-digital converter (not shown) digitizes the signal, all according to conventional methods.

Finally, inside the case 11 a light source 17 is housed, in particular a flash light adapted for generating bioelectric activity of the retina, with the help of diffuser means represented by the lens 12, or a continuous light adapted to stimulate the retina photoreceptors and the cells related therewith.

The device according to the invention therefore operates in the following manner. Once a suitable cleaning of the skin has been carried out at the level of the eye socket and eyelid, an electroconductive gel, of per se known characteristics, is applied on the skin itself. In this way, the electrical contact with the electrodes of the device is promoted.

At this point, the handpiece 1 is rested with the front end 11a in contact with the patient's skin, substantially coaxially to the visual axis of the eye E. Then the light stimulus is activated by the source 17, under the control of a software system that, for example installed on the PC, controls the light stimulation and the procedure of acquisition of the bioelectric response of the retina. The software has general characteristics analogous to those of known systems for ERG recording with corneal or other different electrodes.

Such a stimulus, nevertheless, will in this case take into account some correctives linked to the specific requirement of making the stimulus also effective through the eyelid, and therefore the intensity of the light, besides being as usually calibrated as a function of the specific examination conditions and regulated as a function of the size (surface area) of the pupil (based on the formula RI=FS*PS where RI=illumination of the retina, FS=intensity of the illumination and PS=size of the pupil), will be increased so as to reproduce an illumination situation perceived by the retina substantially equivalent to the current one with the eye open.

For example, a stimulus of intensity equal to 3.0 Cd/m$^2$·Sec (average base of current clinical practice with known devices) increased by 0.52 Ulog, can be capable of ensuring a stimulus perceived to be fully satisfactory. Of course, these are only example data, able to undergo variations and optimisations as a function of the different circumstances in which the clinical examination is being carried out, as well as the different types of patients. Similar considerations apply for the scotopic functionality of the human eye for which the light intensity will be equally increased. In fact, applying a stimulus of scotopic intensity and increasing it gradually until a bioelectric response of the photoreceptors (late receptor potential) is obtained, it will be possible to derive the attenuation of the light stimulus through the closed eyelid, so as to permit to increase of a known amount, and in a proportional way, the light stimulus necessary to obtain a photopic bioelectric response.

In synchrony with the stimulus, the system acquires the sampled signal intended for processing (bioelectric response) by the electrodes incorporated in the handpiece. Since the eyelid is a semi-transparent thin wall, this in fact being the surprising intuition at the basis of the present invention, the light still reaches the retina and stimulates it in a manner suitable for allowing the generation of a bioelectric signal and its detection by the electrodes embodied within the device.

As mentioned above, the device is associated or can be associated with processing means such as a personal computer 2 with a software system suitable for simultaneously managing the generation of a sequence of light stimuli through the source 17 and the consequent recording of the biopotential.

The recording of the ERG and VEP thus obtained will therefore usable as an effective diagnostic support for important eye pathologies such as Age-related Macular Degeneration, Diabetic Retinopathy and retinal dysfunctions and degenerations in general, with the essential advantage that the speed and non-invasiveness of the technique make it suitable for facilitating the screening of large populations of patients. At the same time, the morphology of the retina and the function of each retinal region can be analysed.

The electrodes in contact with the eyelid do not, however, interfere with the visual stimulus presented to the patient, being positioned outside of the visual area (defined as "from white to white" area the limits of which are determined by the border between the transparent cornea and the white sclera). Moreover, better contact impedance between electrode and patient, and therefore a more reliable contact, is obtained with respect to corneal electrodes in contact with the open eye. The possible refractive problems connected to the use of corneal electrodes, or irritation problems of the eye surface exposed to contact with the electrodes are also avoided, and it is possible to record the bioelectrical signal of the retina with very high signal/noise ratio, and also for this reason the time taken for the examination is substantially reduced (reducing the number of samplings needing to be carried out).

The software on the processing means, as well as allowing the processing, displaying and printing of the biopotential recorded with known methods and purposes, can allow the medical operator to easily have results of a comparison between the values detected and the expected values (and considered "normal") for the specific patient under examination. For this purpose it is possible to use databases obtained from clinical studies that indeed permit to detect whether the patient under examination is in accordance with the reference values, in relation to various and different pathologies, or instead differs from them by more than a standard deviation value. The values detected include the amplitude measurement (A=μV) of the bioelectric response generated by the retina following light stimuli and the implicit response time (T=ms). The size of the bioelectric response can be evaluated in retinal pathologies of various origin and nature in reference to normal values for clinical diagnostics.

The implicit time, on the other hand, is the time in which the light stimulus applied to the retina, which due to the properties thereof is transformed into bioelectric response. Such a photoelectric transformation time carried out by the various retinal cellular photoreceptor complexes does not depend on the possible attenuation of light carried out by the eyelid and therefore is a very stable piece of data. On the other hand, different retinal pathologies carry out a delay in the photoelectric transformation process of the light stimulus, a delay that can be easily evaluated.

Such clinical studies can be carried out using the device described above in combination with an Optical Coherence Tomography (OCT) apparatus.

Thanks to the greater reliability of measurement able to be obtained according to the invention, a measurement which moreover is less linked, due to the particular modes of use of the device, to the ability of the medical operator, as well as more independent from disturbances, voluntary or otherwise, of the patient, the comparison of the response with the normal reference data correlated to the age of the subject can be carried out more precisely and safely. Of course, it is possible to create an archive of results obtained, for the purposes of subsequent diagnosis, and thus monitor the evolution of the pathology and the effectiveness of pharmacological treatment over time.

Various constructive and size modifications can be made to the device described above, in particular in relation to the position and to the structure of the light diffuser in order to optimise the quantity and the quality of the diffused light. The external structure (case 11) will be insulated and hermetic with respect in particular to the permeability of liquids or gels. The handpiece can also contain all of the control electronics necessary for operation inside it, and in this case the device can be configured as completely autonomous also in terms of the recording of data, subject to the provision of suitable communication ports (for example USB ports) for data transfer.

Other variants and/or modifications can be brought to the device and method for recording to the ERG response of an eye through the eyelid according to the present invention, without for this reason departing from the scope of protection of the invention itself as defined by the attached claims.

The invention claimed is:

1. A device for recording signals which are a function of the ERG and VEP bioelectrical response of an eye of a patient in response to a visual stimulus, comprising:
    a light emission means configured to generate said stimulus,
    a sensor means to detect said bioelectric response configured to be placed in contact with the patient, the device being configured to communicate with a processing means
    said processing means configured to control said light emission means to manage the emission of said stimulus and to receive and process a detection signal emitted by said sensor means,
    wherein said sensor means are arranged on at least one eyepiece configured to abut with a patient's eye with the eyelid closed, in contact at least partially with said eyelid, and said light emission means and said processing means are configured such that said bioelectric response is detected by said sensor means when said stimulus is perceived through the closed eyelid,
    wherein said light emitting means and said sensor means are disposed within an elongated handpiece configured to be gripped by a medical operator,
    wherein said sensor means for each handpiece comprises an active electrode and a reference electrode both arranged on said eyepiece in correspondence with an axial end of the handpiece, said electrodes being concentrically arranged on a ring of said eyepiece and said ring being configured to contact the face of the patient around the eye socket, and
    wherein said both concentric electrodes are radially spaced from a center axis at the axial end of the device, said reference electrode being radically spaced greater from the central axis than said active electrode.

2. The device according to claim 1, wherein said electrodes are circuitally connected with a differential amplifier outputting a detection signal adapted to be processed by said processing means.

3. The device according to claim 1, wherein said handpiece comprises an ergononomically shaped frame to be gripped by a medical operator.

4. The device according to claim 1, comprising said processing means onboard said handpiece.

5. The device according to claim 1, comprising said processing means in a remote position with respect to said handpiece and communicating therewith via wire means or wireless systems.

6. The device according to claim 1, wherein said eyepiece comprises light diffuser means for diffusing the light emitted by said light emission means.

7. A method for recording signals which are a function of the ERG and VEP bioelectrical response of an eye of a patient in response to a visual stimulus, the method providing the emission of a light stimulus and the detection of the bioelectric response in response to said stimulus, the method comprising:
    providing the device of claim 1,
    at least partially contacting the eye socket of the patient with the eyepiece of said device,
    providing visual stimulus with the device to the eye of the patent with the eyelid closed, and
    detecting the bioelectric response of the patent with the device in contact with the closed eyelid, the stimulus being such that said bioelectric response is detected by the device when the stimulus is perceived by the patient through the closed eyelid.

* * * * *